United States Patent [19]
Jackwood et al.

[11] Patent Number: 5,605,792
[45] Date of Patent: Feb. 25, 1997

[54] INFECTIOUS BURSAL DISEASE VIRUS VP2 FUSION PROTEIN EXPRESSED BY BACULOVIRUS, USE AS DIAGNOSTIC

[75] Inventors: Daral J. Jackwood; Renee J. Jackwood, both of Wooster, Ohio

[73] Assignee: The Ohio State University Research Foundation, Columbus, Ohio

[21] Appl. No.: 445,300

[22] Filed: May 19, 1995

Related U.S. Application Data

[62] Division of Ser. No. 148,252, Nov. 4, 1993, abandoned.

[51] Int. Cl.$^6$ .............................. C12Q 1/70; C12N 7/01; C07K 19/00
[52] U.S. Cl. ...................... 435/5; 435/320.1; 435/235.1; 435/69.1; 530/350
[58] Field of Search ............................. 424/192.1, 204.1; 435/320.1, 235.1, 5; 530/350

[56] References Cited

PUBLICATIONS

Burkhardt E, Müller H (1987), Susceptibility of chicken blood lymphocytes and monocytes to infectious bursal disease virus (IBDV), Arch Virol 94:297–303.

Cervantes H N, Munger L L, Ley D H, Ficken M D (1988), Staphylococcus–induced gangrenous dermatitis in broilers, Avian Dis 32:140–142.

Hofacre C L, French J D, Fletcher O J (1986), Subcutaneous clostridial infection in broilers, Avian Dis 30:620–622.

Rosenberger J K, Gelb Jr. J (1977), Response to several avian respiratory viruses as affected by infectious bursal disease virus, Avian Dis 22:95–105.

Rosenberger J K, Klopp S, Eckroade R J, Krauss W C (1975), The role of the infectious bursal agent and several avian adenoviruses in the hemorrhagic–aplastic–anemia syndrome and gangrenous dermatitis, Avian dis 19:717–729.

Wyeth P J (1975), Effect of infectious bursal disease on the response of chickens to s typhimurium and E coli infections, Vet Rec 96:238–243).

MüH, Scholtissek C, Becht H (1979), The genome of infectious bursal disease virus consists of two segments of double–stranded RNA, J Virol. 31:584–589.

Hudson P J, McKern N M, Power B E, Azad A A (1986), Genomic structure of the large RNA segment of infectious bursal disease virus, Nucleic Acid Res 14:5001–5012.

Morgan M M, Macreadie I G, Harley V R, Hudson P J, Azad A A (1988), Sequence of the small double–stranded RNA genomic segment of infectious bursal disease virus and its deduced 90–kDa product, Virol 240–242.

Azad A A,Jagadish M N, Fahey K J (1987), Deletion mapping and expression in *Escherichia coli* of the large genomic segment of a birnavirus, Virol 161:145–152).

Bayliss C D, Spies K, Peters R W, Papageorgiou A, Müller H, Boursnell M E G (1990), A comparison of the sequences of segment A of four infectious bursal disease virus strains and identification of a variable region in VP2, J Gen Virol 71:1303–1312).

Azad A, Macreadie I, Vaughan P, Jagadish M, McKern N, Heine H G, Failla P, Ward C (1990), Full protection against an immunodepressive viral disease by a recombinant antigen produced in yeast, Vacc 90:59–62.

Bayliss C D, Peters R W, Cook J K A, Reece R L, Howes K, Binns M M, Boursnell M E G (1991), A recombinant fowlpox virus that expresses the VP2 antigen of infectious bursal disease virus induces protection against mortality caused by the virus, Arch Virol 120:193–205.

Lackow V A, Summers M D (1988), Trends in the development of baculovirus expression vectors, Biotech 6:47–56.

Becht, H, Müller H K (1988), Comparative studies on structural and antigenic properties of two serotypes of infectious bursal disease virus, J Gen Virol 69:631–640.

Vakharia V N, Snyder D B, He J, Edwards G H, Savage P K, Mengel–Whereat S A (1993), Infectious bursal disease virus structural proteins expressed in a baculovirus recombinant confer protection in chickens, J Gen Virol 74:1201–1206).

Öppling V, Müller H, Becht H (1991), Heterogeneity of the antigenic site responsible for the induction of neutralizing antibodies in infectious bursal disease virus, Arch Virol 119:211–223.

Crisman J M, Jackwood R J, Lana D P, Jackwood D J (1992), Evaluation of VP2 epitopes of infectious bursal disease virus using in vitro expression and radioimmuno–precipitation, Arch Virol 128:333–344.

Ismail N M, Saif Y M, Wigle W L, Havenstein G B, Jackson C (1990), Infectious bursal disease virus variant from commercial leghorn pullets, Avian Dis 34:141–145.

Saif Y M, Jackwood M W, Jackwood DH, (1987), Relatedness of the IBDV vaccine strains and field strains, Proc 36th Western Poultry Disease Conference, University of California Cooperative Extension, Davis C A pp. 100–111).

Rosenberger JK, Cloud SS, Metz A (1987) Use of infectious bursal disease virus variant vaccines in broiler and broiler breeders, Proc Western Poultry Disease conference, Davis, CA pp. 105–106.

Jackwood D H, Saif Y M, Hughes J H (1986), Replication of infectious bursal disase virus in continuous cell lines, Avian Dis 31:370–375.

Lana D P, Beisel C E, Silva R F (1992) Genetic mechanisms of antigenic variation in infectious bursal disease virus: analysis of a naturally occuring variant virus, Virus Genes 6–3:247–259.

Summers, M. D., Smith, G. E. (1988), A manual of methods for baculovirus vectors and insect cell culture procedures, Texas Agricultural Experimental Station Bulletin No. 1555, Texas Agricultural Experimental Station, College Station, Texas.

Jackwood D J, Kibenge F, Mercado C, (1989), Detection of infectious bursal disease virus by using cloned cDNA probes, J Clin Microbiol 27:2437–2443.

Jackwood, D. H., Saif, T. M. (1987), Antigenic diversity of infectious bursal disease virus, Avian Dis. 31:766–770.

*Primary Examiner*—Mary E. Mosher
*Assistant Examiner*—Ali Salimi
*Attorney, Agent, or Firm*—Emch, Schaffer, Schaub & Porcello

[57] ABSTRACT

The present invention relates to the expression of the variable region of a VP2 protein from infectious bursal virus disease by recombinant baculovirus, diagnostic assays and vaccines containing the same.

6 Claims, No Drawings

INFECTIOUS BURSAL DISEASE VIRUS VP2 FUSION PROTEIN EXPRESSED BY BACULOVIRUS, USE AS DIAGNOSTIC

This is a divisional of application Ser. No. 08/148,252 filed Nov. 4, 1993, now abandoned.

TECHNICAL FIELD

The present invention relates to the poultry industry, and in particular, poultry viruses and vaccines therefrom.

The present invention relates to recombinant DNA-directed synthesis of certain proteins and the cell lines which express the recombinant DNA and proteins. More particularly, the present invention relates to the expression of the variable region of a truncated VP2 protein from infectious bursal disease virus by a recombinant baculovirus.

The present invention is useful for diagnosing infectious bursal disease in poultry and as an infectious bursal disease vaccine containing the variable region of the truncated VP2 protein.

BACKGROUND OF THE INVENTION

Infectious bursal disease, also known as Gumboro disease, infects poultry world-wide and is responsible for many losses in the poultry industry. Infectious bursal disease is known to be caused by a virus, the infectious bursal disease virus (IBDV). This disease often affects poultry as young as one to six weeks old and causes inflammation, diarrhea, muscular hemorrhaging, bleeding, damage to the immune system and necrosis of the Bursa of Fabricii.

The immunosuppression results from a depletion of the chicken's B lymphocytes (Burkhardt E, Müller H (1987) Susceptibility of chicken blood lymphocytes and monocytes to infectious bursal disease virus (IBDV). Arch Virol 94:297–303). Secondary infections are commonly associated with infectious bursal disease (Cervantes HM, Munger LL, Ley DH, Ficken MD (1988) Staphylococcus-induced gangrenous dermatitis in broilers. Avian Dis 32:140–142; Hofacre CL, French JD, Fletcher OJ (1986) Subcutaneous clostridial infection in broilers. Avian Dis 30:620–622; Rosenberger JK, Gelb Jr. J (1977) Response to several avian respiratory viruses as affected by infectious bursal disease virus. Avian Dis 22:95–105; Rosenberger JK, Klopp S, Eckroade RJ, Krauss WC (1975) The role of the infectious bursal agent and several avian adenoviruses in the hemorrhagic-aplastic-anemia syndrome and gangrenous dermatitis. Avian Dis 19:717–729; Wyeth PJ (1975) Effect of infectious bursal disease on the response of chickens to *s typhimurium* and *E coli* infections. Vet Rec 96:238–243). The IBDV virion consists of two segments of double-stranded RNA (Müller H, Scholtissek C, Becht H (1979) The genome of infectious bursal disease virus consists of two segments of double-stranded RNA. J Virol 31:584–589). One segment, called segment A, encodes a fusion protein which is cleaved into the structural proteins VP2, VP3 and VP4 (Hudson PJ, McKern NM, Power BE, Azad AA (1986) Genomic structure of the large RNA segment of infectious bursal disease virus. Nucleic Acid Res 14:5001–5012). The other segment, segment B, encodes the putative vital polymerase VP1 (Morgan MM, Macreadie IG, Harley VR, Hudson PJ, Azad AA (1988) Sequence of the small double-stranded RNA genomic segment of infectious bursal disease virus and its deduced 90-kDa product. Virol 240–242). A neutralizing monoclonal antibody (MAb) binding site was mapped to a region of VP2 between amino acids 206 and 350 (Azad AA, Jagadish MN, Fahey KJ (1987) Deletion mapping and expression in *Escherichia coli* of the large genomic segment of a birnavirus. Virol 161:145–152). Analysis of the nucleic acid and predicted amino acid sequences among several strains of IBDV has revealed an area of high variability among strains of IBDV within this region (amino acids 239–332) (Bayliss CD, Spies K, Peters RW, Papageorgiou A, Müller H, Boursnell MEG (1990) A comparison of the sequences of segment A of four infectious bursal disease virus strains and identification of a variable region in VP2. J Gen Virol 71:1303–1312).

Several expression systems have been utilized to produce the IBVD VP2 protein. Azad et al. (Azad A, Macreadie I, Vaughan P, Jagadish M, McKern N, Heine HG, Failla P, Ward C (1990) Full protection against an immunodepressive viral disease by a recombinant antigen produced in yeast. Vacc 90:59–62) expressed VP2 as a fused and non-fused protein in *Escherichia coli*. Both expression products were poor immunogens. A recombinant fowlpox virus expressing VP2 protected birds challenged with IBDV against mortality, but not against damage to the bursa (Bayliss CD, Peters RW, Cook JKA, Reece RL, Howes K, Binns MM, Boursnell MEG (1991) A recombinant fowlpox virus that expresses the VP2 antigen of infectious bursal disease virus induces protection against mortality caused by the virus. Arch Virol 120:193–205). A recombinant VP2 protein produced in yeast induced neutralizing antibodies and protected progeny chickens from IBDV challenge (Hofacre et al., 1986, supra). IBDV antigen could not be detected in the bursa of progeny from birds immunized with the recombinant yeast protein following challenge with the virus. Recombinant proteins expressed in baculovirus have been produced in amounts of 1 to 500 mg/ml (Luckow VA, Summers MD (1988) Trends in the development of baculovirus expression vectors. Biotech 6:47–56; Smith GE, Summers MD, Fraser MJ (1983) Production of human beta interferon in insect cells infected with a baculovirus expression vector. Mal Cell Biol 3:2156–2165). This expression system utilizes many of the protein modification, processing and transport systems that occur in higher eukaryotic species.

Immunologic studies involving IBDV have suggested that VP2 contains a conformational dependent neutralizing epitope which could be used to distinguish serotypes (Becht, H, Müller HK (1988) Comparative studies on structural and antigenic properties of two serotypes of infectious bursal disease virus. J Gen Virol 69:631–640). A monoclonal antibody (1/A6) against VP2 has been mapped to a small highly variable region (Azad et al., 1987, supra).

IBDV proteins have also been expressed using baculovirus (Vakharia VN, Snyder DB, He J, Edwards GH, Savage PK, Mengel-Whereat SA (1993) Infectious bursal disease virus structural proteins expressed in a baculovirus recombinant confer protection in chickens. J Gen Virol 74:1201–1206), wherein it was reported that these proteins reacted with IBDV specific monoclonal antibodies and resembled the native viral proteins. Seventy-nine percent of the birds vaccinated using these baculovirus expressed VP2, VP3 and VP4 proteins were protected against a homologous IBDV challenge.

In addition, other vaccines have been produced in an attempt to control infectious bursal disease. These vaccines, developed containing either live or attenuated viruses, or cultures of the bursal cells for example, while protecting the poultry from mortality, still cause symptoms of infectious bursal disease in the vaccinated poultry. These symptoms included growth retardation and injury to the Bursa of Fabricii. Another problem with the prior art vaccines is that there are increasing outbreaks of infectious bursal disease which are not prevented from occurrence by any of the prior art vaccines, Another problem is the immunization itself of the poultry. Both the timing and method of administration of the vaccine continue to present problems. In particular, problems arise with attempts to vaccinate newly hatched poultry since such newly hatched poultry are often hatched with maternal antibodies to the infectious bursal disease (either to previous infections or vaccination of the hen against the infectious bursal disease). Thus, the time period for vaccination becomes critical. It is important to effectively and rapidly vaccinate large numbers of poultry. The mass immunization of poultry is best effected through such methods of spraying or in the drinking water of the poultry.

Therefore, there are still problems in the prior art to determine the causes of new outbreaks of infectious bursal disease and to develop a vaccine which is resistant to both the known strains and further strains of infectious bursal disease. There is a further need to determine a method of preventing such further outbreaks through vaccination of the affected population. There is a further need to develop a vaccine which can be administered in a timely manner, both by achieving vaccination at the critical times in the poultry's life and by mass immunization to rapidly inoculate the entire poultry population. There is still a further need to provide a vaccine which does not cause symptoms of infectious bursal disease to occur in the vaccinated poultry.

DISCLOSURE OF INVENTION

According to the present invention, a portion of VP2 which contains the highly variable region was isolated and expressed in a baculovirus system. Further, according to the present invention, there is disclosed cells transfected with a DNA sequence in coding a VP2 fusion protein and capable of expressing said protein.

The production of IBDV antigen for diagnostic assays from whole viral particles is a costly endeavor. The VP2 fusion protein expressed by a recombinant baculovirus of the present invention is useful as an improved diagnostic reagent in, for example, ELISA, agar gel precipitin assay or other assays which detect IBDV antibodies in chickens. This fusion protein is also useful for further evaluating the neutralizing epitopes of the VP2 protein.

In particular, a portion of the VP2 gene from the variant A strain of infectious bursal disease virus was ligated into the pAc360 transfer vector and transfected into baculovirus. Recombinant baculoviruses were identified using dot blot hybridization. According to one aspect of the present invention, one recombinant baculovirus, 9A5, expressed a 56.7 kDa fusion protein. Radioimmunoprecipitation was used to confirm the identity of this protein. Polyclonal antibodies against the MD strain of IBDV immunoprecipitated the $^{35}$S-methionine labeled fusion protein. The fusion protein was expressed from suspension cultures of Sf9 insect cells in quantities of at least about and often greater than 100 mg/liter of cell culture media. Specific-pathogen-free white leghorn chickens were inoculated twice with $5\times10^6$ or $1\times10^7$ Sf9 insect cells that were infected with recombinant baculovirus expressing the VP2 fusion protein. Neutralizing antibody titers were observed in these birds following the second inoculation using a virus neutralization assay.

The present invention, thus, relates to novel cell lines such as recombinant baculovirus 9A5, which express a VP2 fusion protein. These novel cells line substantially enhance the availability of VP2 fusion protein.

One object of the present invention is to provide purified forms of the VP2 fusion protein. An additional object of the present invention is to provide purified forms of the VP2 fusion protein and novel cell lines expressing the VP2 fusion protein, both which are valuable in the production of antigens for diagnostic assays. The VP2 fusion protein and the cell lines expressing this protein are also valuable in the production of a new and improved vaccine against infectious bursal disease.

Other objects, advantages and novel features of the present invention will be presented in the following detailed description and examples of the present invention.

DESCRIPTION OF THE INVENTION

The present invention has made it possible to express a VP2 structural protein in baculovirus. Until the present invention, no one has produced a fusion protein of a VP2 protein and baculovirus polyhedrosis protein.

The recombinant baculovirus 9A5 of the present invention expresses a 56.7 kDa fusion protein. The VP2 gene fragment is 944 bases in length and does not include the initial 300 bases which results in the absence of 100 amino acids located at the amino terminus of native VP2. The absence of these amino acids does not interfere with the proper folding of the variable region.

The elicitation of neutralizing antibodies according to the present invention shows that proper folding of the VP2 fusion protein occurred. However, the titers of these neutralizing antibodies were lower in most birds and absent in others. As a result of this protein being a fusion protein, 14 amino acids at the amino terminus and 184 amino acids at the carboxy terminus flanked the 314 amino acids of the VP2 protein. The total addition of 198 irrelevant amino acids may have affected the conformational dependent epitope and resulted in the observed low neutralizing titers. However, it is believed that there are additional conformationally dependent neutralizing epitopes (Oppling V, Muller H, Becht H (1991) Heterogeneity of the antigenic site responsible for the induction of neutralizing antibodies in infectious bursal disease virus. Arch Virol 119:211–223; Crisman JM, Jackwood RJ, Lana DP, Jackwood DJ (1992) Evaluation of VP2 epitopes of infectious bursal disease virus using in vitro expression and radioimmunoprecipitation. Arch Virol 128:333–344). The inventors herein believe that it is possible that other neutralizing epitopes are required to obtain high neutralizing antibody titers. Vakharia et al., supra, used baculovirus to express the entire VP2 protein in addition to the VP3 and VP4 proteins of IBDV and obtained an average virus neutralizing antibody titer of 1024 in chickens. The inventors thus believe that more than just the neutralizing epitope on VP2 described by Azad et al., supra, is needed to elicit adequate immunity to IBDV. No one until the present inventors herein have developed a recombinant baculovirus expressing the variable region of the VP2 gene from the variant A strain of infectious bursal disease.

The principles for the present invention will be explained by this detailed description of the preferred embodiment together with the following examples.

Identification of the VP2 Fusion Protein

The 944 bp PstI/BalI fragment represents bases 434 through 1377 of the VP2 gene which contains the variable sequence region (Bayliss et al, 1990, supra). The recombinant transfer vector, p360v17, was identified using restriction enzyme analysis and transfected into baculovirus DNA.

Recombinant baculovirus plaques that were not refractive when illuminated by a fiber optics light source (Dolan - Jenner Industries, Inc., Woburn, Mass.) were selected. Dot blot hybridization confirmed the presence of the 944 bp fragment in recombinant viruses following each plaque purification.

To determine if the recombinant viruses were expressing the VP2 fusion protein, vital proteins were metabolically labeled in Sf9 cells at 48 hours post inoculation (PI) with $^{35}$S-methionine and analyzed by 12% SDS-PAGE (O'Reilly DR, Miller LK, Luckow VA (1992) Baculovirus expression vectors: a laboratory manual. W. H. Freeman and Company, New York). A protein with the size of the VP2 fusion protein (56.7 kDa) was observed in recombinant baculovirus 6A3 and 9A5. A similar size protein was not observed in the wild type baculovirus. Furthermore, the polyhedrosis protein (32 kDa) was observed in the wildtype virus, but not in the recombinant viruses.

Polyclonal chicken serum against the variant IBDV strain, MD, was used to verify the authenticity of the 56.7 kDa protein in a radioimmunoprecipitation assay. Immunoprecipitated proteins were separated by 12.5% SDS-PAGE and visualized using autoradiography. A 56.7 kDa protein band was observed. This size band corresponded to that of the fusion protein. No proteins were observed in the lanes containing protein samples from the wildtype baculovirus and mock-infected cell controls.

The quantity of VP2 fusion protein in Coomassie blue stained gels was determined by densitometer analysis and direct comparison to known BSA quantities. Expressed recombinant protein was produced in quantities>100 mg/liter of insect media. Sf9 cells inoculated with recombinant 9A5 at a MOI of 0.02 and harvested 72 hours later produced 30 ug of the VP2 fusion protein in $1\times10^7$ cells. Sf9 cells inoculated with recombinant 9A5 at a MOI of 0.2 and harvested at 72 hours PI produced>600 ug of the VP2 fusion protein in $1\times10^7$ cells. The intensity of recombinant 9A5 protein bands stained with Coomassie blue was greater in samples harvested at 72 hours than at 48 hours.

Immunogenic Properties of the VP2 Fusion Protein

The ability of the VP2 fusion protein to elicit neutralizing antibodies was determined by immunizing specific pathogen-free white leghorn chickens with Sf9 cells infected with recombinant 9A5 baculovirus. Sera from these birds were analyzed using a virus neutralization assay.

Titers of virus neutralizing antibodies were variable. Neutralizing antibodies were first detected at three weeks following the initial inoculation. Two weeks after the booster inoculation, the following neutralizing antibody titers were determined in assays utilizing the cell culture adapted variant A strain of IBDV as antigen: two birds had titers of 320, one bird each had titers of 40, 20, 14 and 10. Four birds inoculated with recombinant 9A5 baculovirus infected Sf9 cells had no detectable antibodies at two weeks after the booster inoculation. Neutralizing antibody titers were similar for assays utilizing cell culture adapted variant IBDV strains IN or MD as antigen. All control bird serum samples were negative for neutralizing antibodies.

Use of VP2 Fusion Protein Useful in the Production of Antigens For Diagnostic Assays The VP2 fusion protein expressed by the recombinant baculovirus 9A5 is an improved diagnostic reagent for such assays as ELISA, agar gel, precipitin assays and other assays which detect IBDV antibodies in chickens. The VP2 fusion protein is also useful for evaluating the neutralizing epitopes of the VP2 protein.

According to one aspect of the present invention, a method for illustrating neutralizing antibodies to infectious bursal disease virus comprises the steps of inoculating an animal susceptible to infectious bursal disease with an effective amount of at least one of the following: 1) a recombinant baculovirus expressing the VP2 fusion protein or 2) the VP2 protein itself.

The concentration of VP2 protein in infected poultry differs from non-infected poultry. The reagent of this invention can be in the form of an absorbent resin having absorbed on a surface thereof an amount of the anti-VP2 fusion protein effective to render the resin reactive. Also, other non-reactive, preferably particulate resins which absorb proteins on an exterior surface thereof, such as those used to immobilize enzymes can be used. The amount of antigen absorbed thereon can range from about 5 to 100 nm/mg of resins and preferably about 25 to 75 nm/mg.

Thus, the present invention also provides for a kit for detecting the presence of a neutralizing antibody to infectious bursal virus disease. The kit preferably comprises a predetermined amount of an infectious disease virus antigen. It is to be understood that the antigen would preferably be labelled with a readily determinable label to aid in the detection of the infectious bursal disease virus. It is also understood that the kit can comprise a container for ease in mixing the sample from the tested poultry with the antigen.

The present invention contemplates the development of diagnostic assays for the determination of the neutralizing IBDV antibody. Those skilled in the art recognize that methods by which such assays are developed and utilized can be employed in the present invention and do not constitute an inventive aspect of the present invention. It is further understood that those skilled in the art will be able to utilize one of the various methods available for labeling antigens in order to perform diagnostic assays, such as competitive ELISA. Various labels or tags including materials such as radioactive iodine and radioactive cobalt, biotin, various enzymes and fluorescing materials. It is understood that the labeled antigen may be supported or unsupported and that such determination can be best made by the practitioner. Further, the standard for any labeled antigen is readily determined either directly or indirectly. In a direct determination, the amount of antibody present in the sample to the labeled antigen is determined directly by determining the amount of the bound material isolating and determining that amount of bound material. An indirect determination evaluation is made of the amount of unbound materials left after a predetermined time. These determinations are compared with a previously established standard such that the presence of the neutralizing antibodies in the affected poultry are measured.

As will be recognized by those skilled in the art after establishing the neutralizing and binding capacity of the antigens, it is seen that the antigens can be used as a basis for diagnostic assays and testing for the presence of infectious bursal disease in poultry populations. Further, fine VP2 fusion can be used to inoculate poultry populations against IBDV infection. It is known to those skilled in the art that the method of inoculation can vary greatly. Such considerations involve the use of either live or inactivated vaccine.

The vaccine may be prepared according to common methods, which are not per se a part of this invention. These methods involve the use of either live or attenuated vaccines.

These methods include heat and chemical killing which allow the vaccinated poultry to develop protective antibodies itself without it coming to the disease. It is also possible to attenuate the viruses using such known methods as serial passage or a cloning of the virus leading sequences of nucleic acids, or site-directed mutagenesis. These methods provide a live non-virulent vaccine. It is understood that those of ordinary skill in the art will be able to determine the actual amount of protection needed and therefore, the level of protection needed by a particular poultry population. The appropriate dosage levels can be readily determined through routine experimentation to deliver the appropriate concentration levels to each poultry population. Further, it is understood that the vaccine may be prepared by incorporation of the virus derivative in an effective carrier either by suspension or mixture or other known methods. The necessary levels of protection can range between one microgram to one milligram. Alternatively, vaccinations carried out over time can be utilized having smaller effective dosages administered to the poultry population. As is understood, the concentration dosage levels needed to effectively inoculate poultry depends on the age and increase in size of each poultry. It is understood that the vaccine comprises the active ingredient and pharmaceutically acceptable carriers or diluents. In preferred embodiments, the carrier or diluents are compatible with the vaccine administration procedures used with mass vaccine administration procedures, such as spraying the animal or the animal's environment or in the animal's drinking water. It is contemplated, however, that the other administration methods such as injections, eye drops (ophthalmically), nose drops (nasally) and the like are also useful with the present invention. In addition, various adjuvants are useful in order to enhance the poultry's immune response to the antigens. These adjuvants are well known to those skilled in the art. Further, stabilizers and other ingredients are contemplated as being useful in preparing an acceptable vaccine for immunization.

The following examples give particular embodiments of the invention and demonstrate the practice and advantages of the present invention. It is understood that the examples are given by way of illustration and are not intended to limit the specification or claims in any manner.

EXAMPLES

Viruses and Antisera

Wildtype baculovirus (*Autographa califonica* nuclear polyhedrosis virus) was propagated in *Spodoptera frugiperda* (Sf9) cells (Invitrogen, San Diego, Calif.). Cell culture-adapted variant IBDV strains IN, MD and A (Ismail NM, Saif YM, Wigle WL, Havenstein GB, Jackson C (1990) Infectious bursal disease virus variant from commercial leghorn pullets. Avian Dis 34:141–145; Saif YM, Jackwood MW, Jackwood DH (1987) Relatedness of the IBDV vaccine strains and field strains. Proc 36th Western Poultry Disease Conference, University of California Cooperative Extension, Davis CA pp.100–111); Rosenberger JK, Cloud SS, Metz A (1987) Use of infectious bursal disease virus variant vaccines in broiler and broiler breeders. Proc Western Poultry Disease Conference, Davis, CA pp. 105–106) were propagated on baby Grivet monkey kidney (BGM-70) cells (Jackwood DH, Saif YM, Hughes JH (1986) Replication of infectious bursal disease virus in continuous cell lines. Avian Dis 31:370–375). Antisera against variant IBDV strain MD was collected from convalescent specific-pathogen-free white leghorn chickens.

Insertion of the VP2 Gene into pAc360 Transfer Vector

The VP2 cDNA was provided by D. P. Lana (National Cancer Institute Frederick Cancer Research and Development Center, Frederick, Md.). The V17 cDNA was 1006 base pairs (bp) and contained bases 380 to 1386 of the VP2 gene (Lana DP, Beisel CE, Silva RF (1992) Genetic mechanisms of antigenic variation in infectious bursal disease virus: analysis of a naturally occurring variant virus. Virus Genes 6-3:247–259). This fragment was ligated into pGem 3Zf(+) (Promega Corporation, Madison, Wis.) (Crisman, et al., supra). The resulting recombinant plasmid (pV-17) was transformed into *Escherichia coli* and plated on Luria agar plates containing 50 ug/ml ampicillin (Sigma Chemical Co., St. Louis, Mo.). An isolated colony was selected and grown in terrific broth (Sambrook J, Fritsch EF, Maniatis T (1989) Molecular cloning: 2 laboratory manual, 2nd edn. Cold Spring Harbor Laboratory Press, New York) containing 50 ug/ml ampicillin. Plasmid DNA was isolated using an alkaline extraction procedure (Sambrook et al., supra).

Plasmid pV-17 was digested with BalI (Promega) and partially digested with PstI (Promega). The DNA fragments were separated by electrophoresis using 1% agarose (FMC Corporation, Rockland, Me.) in TBE buffer (89 mM Tris base [pH 8.0], 89 mM boric acid, 2 mM EDTA) (Amresco, Solon, Ohio). A 944 bp fragment was cut from the gel and isolated into TBE buffer using an electro-eluter (Bio-Rad Laboratories, Richmond, Calif.) according to the manufacturer's instructions. The 944 bp fragment was extracted with phenol and chloroform, precipitated using ethanol and after centrifugation was suspended in double distilled $H_2O$. The protruding 3' PstI end was removed using T4 DNA polymerase (Stratagene, LaJolla, Calif.) (Sambrook et al., supra). A BamHI 10 mer linker was ligated onto each end using T4 Ligase (Bethesda Research Laboratories, Gaithersburg, Md.) as described in Sambrook et al., supra. The fragments were then digested to completion with BamHI (Promega).

Removal of linker fragments and isolation of the 954 bp fragment was performed by electrophoresis using 1.25% SeaPlaque low gelling temperature agarose (FMC Corporation) in TAE (40 mM Tris-acetate [ph 8.0], 1 mM EDTA) (Amresco). The resulting 954 bp fragment was excised from the gel and ligated into the transfer vector using an in-gel ligation procedure (Ausubel FM, Brent B, Kingston RE, Moore DD, Seidman JG, Smith JA, Struhl K (1992) Short protocols in molecular biology, 2nd edn. Greene Publishing Associates and John Wiley & Sons, New York).

Prior to ligation, the pAc360 vector was digested with BamHI (Promega) and treated with shrimp alkaline phosphatase (United States Biochemical Corporation, Cleveland, Ohio). The treated pAc360 DNA was extracted with phenol and chloroform, precipitated using ethanol and resuspended in TE (10 mM Tris-HCl [pH 7.6], 1 mM EDTA). Ligation reaction products were transformed into *E. coli* Max Efficiency DH5α™ competent cells (Bethesda Research Laboratories) according to the manufacturer's instructions. *E. coli* were plated on Luria agar plates containing 50 ug/ml ampicillin (Sigma). Selected colonies were grown in terrific broth with 50 ug/ml ampicillin. Plasmid DNA from these colonies was isolated using a mini-prep plasmid extraction procedure (Sambrook et al., supra). Restriction enzymes BamHI, HindIII, PstI and SalI were used to confirm the orientation of the VP2 fragment.

Transfection and Selection of Recombinant Virus

Transfection was conducted as described (MAXBAC™ baculovirus expression system, Invitrogen). Recombinant plaques were identified visually and prepared for dot blot hybridization (Summers MD, Smith GE (1988) A manual of methods for baculovirus vectors and insect cell culture procedures. Texas Agricultural Experimental Station bulletin no. 1555. Texas Agricultural Experimental Station, College Station, Tex.). A 612 bp PstI/BalI fragment within the 944 bp fragment was radiolabeled using $^{32}$P-dCTP (ICN Radiochemicals, Irvine, Calif.) and nick-translation (Bethesda Research Laboratories). Dot blot hybridization was conducted (Jackwood DJ, Kibenge F, Mercado C, (1989) Detection of infectious bursal disease virus by using cloned cDNA probes. J Clin Microbiol 27:2437–2443). Positive baculoviruses which contained the VP2 gene fragment were plaque purified an additional two times. Following each plaque purification, hybridization was used to confirm the presence of the VP2 gene fragment. Recombinant baculoviruses were propagated on Sf9 cells for 48 hours. Viral proteins were visualized using 12% SDS-PAGE and Coomassie blue staining (O'Reilly et al., supra). These proteins were also metabolically labeled with $^{35}$S-methionine and analyzed using 12% SDS-PAGE.

The recombinant baculovirus designated 9A5 was propagated at a multiplicity of infection of 0.02 or 0.2 in Sf9 cells for 72 hours. Cells were propagated in suspension cultures as described in O'Reilly et al., supra. At 72 hours post infection, the Sf9 cells were counted to determine cell density and then homogenized and stored at −70° C. Following 12% SDS-PAGE, quantities of the VP2 fusion protein were determined using a densitometer (Bio Rad, Richmond, Calif.). Since bovine serum albumin (BSA) was similar in size to the VP2 fusion protein, known quantities of BSA were separated by electrophoresis and used to prepare a standard curve. BSA samples were used at the following quantities: 20 ug, 10 ug, 5 ug, 2.5 ug and 1 ug. Linear regression analysis of the absorption readings was used to determine the quantity of VP 2 fusion protein.

Radioimmunoprecipitation

VP2 fusion protein was $^{35}$S-methionine labeled (O'Reilly et al., supra). Cells infected with 9A5 were lysed using a double-detergent lysis buffer with protease inhibitors (50 mM Tris-HCl [pH 8.0], 150 mM NaCl, 0.02% sodium azide, 0.1% SDS, 100 ug/ml phenylmethylsulfonyl, 1 ug/ml pepstatin, 0.5 ug/ml leupeptin, 1% Nonidet P-40). A 5 ul volume of lysate was mixed with 5 ul polyclonal MD antiserum. Incubation was at 4° C. for 3 hours. Following incubation, the mixture was combined with 2 ul of polyclonal rabbit anti-chicken serum (Sigma Chemical Company) and incubated at 4° C. for 1 hour. This mixture was added to 100 ul of a 1:1 (v/v) mixture of Sepharose A and NET buffer (50 mM Tris-HCL, [pH 8.0]; 0.14M NaCl; 5 mM EDTA; 0.05% (v/v) Nonidet P-40) and shaken gently for 1.25 hours at 4° C. The mixture was washed three times with NET buffer and suspended in SDS-loading buffer. Samples were analyzed using 12.5% SDS-PAGE. Gels were vacuum dried and then exposed to X-Omat AR film (Eastman Kodak Company, Rochester, N.Y.).

Immunogenicity of Baculovirus Expressed VP2

Six-week-old specific-pathogen-free white leghorn chickens, were used to determine the immunogenicity of the expressed VP2 fusion protein. Ten birds were inoculated subcutaneously with 1×10$^7$ recombinant 9A5 baculovirus-infected Sf9 cells emulsified in Freund's complete adjuvant (DifCo Laboratories, Detroit, Mich.). Nine control birds were inoculated subcutaneously with PBS emulsified in Freund's complete adjuvant (Difco Laboratories). Birds were injected again two weeks later with the corresponding inoculum emulsified in Freund's incomplete adjuvant (Difco Laboratories). Blood samples were taken at 0, 14, 21, and 28 days after the initial injection. Sera from these samples were analyzed by a constant-virus varying-antibody neutralization assay conducted in BGM-70 cells as described (Jackwood DH, Saif TM (1987) Antigenic diversity of infectious bursal disease virus. Avian Dis 31:766–770) using the IN or MD IBDV strains as antigen.

Although the invention has been described with regard to its preferred embodiments, which constitute the best mode presently known to the inventors, it should be understood that various changes and modifications, as would be obvious to one having ordinary skill in the arts, may be made without departing from the scope of the invention, which is set forth in the claims appended hereto.

We claim:

1. A diagnostic composition comprising a diagnostically acceptable carrier and a fusion protein antigen, wherein the fusion protein antigen comprises a 314 amino acids sequence encoded by the PstI-BalI fragment of the VP2 gene of infectious bursal disease virus (IBDV) variant A, said PstI-BalI fragment containing bases 434–1377 of the VP2 gene, and said fusion protein antigen further comprises sequences from the baculovirus polyhedrin protein encoded by a PAC360 vector.

2. The diagnostic composition of claim 1, wherein the fusion protein antigen is absorbed on a resin.

3. A kit for detecting the presence of antibodies to IBDV, which comprises a container and the diagnostic composition of claim 1.

4. A method for detecting IBDV VP2 antibodies in the serum of an animal, which comprises the steps of:

(a) binding antibodies present in a sample of the serum of an animal to a fusion protein antigen, wherein the fusion protein antigen comprises a 314 amino acids sequence encoded by the PstI-BalI fragment of the VP2 gene of (IBDV) variant A, said PstI-BalI fragment containing bases 434–1377 of the VP2 gene, and said fusion protein antigen further comprises sequences from the baculovirus polyhedrin protein encoded by a PAC360 vector; and (b) directly or indirectly determining the amount of antibody bound by said antigen.

5. The method of claim 4, wherein the method of determining is enzyme linked immunoassay or radioimmunoassay.

6. A method for diagnosing exposure of an animal to IBDV, comprising the steps of:

(a) binding antibodies present in a sample of the serum of the animal to a fusion protein antigen, wherein the fusion protein antigen comprises a 314 amino acids sequence encoded by the PstI-BalI fragment of the VP2 gene of (IBDV) variant A, said PstI-BalI fragment containing bases 434–1377 of the VP2 gene, and said fusion protein antigen further comprises sequences from the baculovirus polyhedrin protein encoded by a PAC360 vector;

(b) separating the bound antibodies from the other serum proteins;

(c) directly or indirectly determining the amount of antibody bound by said antigen, and (d) comparing the amount of antibody bound from the animal to the amount bound from a corresponding sample from an uninfected animal, wherein an increased amount indicates the exposure to IBDV.

* * * * *